(12) United States Patent
Gertlowski et al.

(10) Patent No.: US 10,279,600 B2
(45) Date of Patent: May 7, 2019

(54) DIRECT PRINTING MACHINE AND METHOD FOR PRINTING CONTAINERS USING DIRECT PRINTING

(71) Applicant: KRONES AG, Neutraubling (DE)

(72) Inventors: Georg Gertlowski, Schierling (DE); Peter Lindner, Langquaid (DE)

(73) Assignee: Krones AG, Neutrabling (DE)

( * ) Notice: Subject to any disclaimer, the term of this patent is extended or adjusted under 35 U.S.C. 154(b) by 0 days.

(21) Appl. No.: 15/753,934

(22) PCT Filed: Aug. 1, 2016

(86) PCT No.: PCT/EP2016/068277
§ 371 (c)(1),
(2) Date: Feb. 20, 2018

(87) PCT Pub. No.: WO2017/032553
PCT Pub. Date: Mar. 2, 2017

(65) Prior Publication Data
US 2018/0264845 A1 Sep. 20, 2018

(30) Foreign Application Priority Data
Aug. 21, 2015 (DE) .................. 10 2015 216 026

(51) Int. Cl.
*B41J 3/407* (2006.01)
*G01N 21/90* (2006.01)
(Continued)

(52) U.S. Cl.
CPC ........... *B41J 3/4073* (2013.01); *B41J 2/0458* (2013.01); *B41J 2/04508* (2013.01);
(Continued)

(58) Field of Classification Search
CPC ...... B41J 3/4073; B41J 2/0458; B41J 11/007; B41J 2/04508; B41J 2/04581;
(Continued)

(56) References Cited

U.S. PATENT DOCUMENTS

| 8,004,667 B2 * | 8/2011 | Kwirandt | B07C 5/3408 250/222.2 |
| 8,823,220 B2 * | 9/2014 | Yman | B23Q 5/28 239/722 |

(Continued)

FOREIGN PATENT DOCUMENTS

| DE | 102004025666 A1 * | 12/2005 | ............. G01N 21/15 |
| DE | 102007025524 A1 | 12/2008 | |

(Continued)

OTHER PUBLICATIONS

ISA European Patent Office, International Search Report Issued in Application No. PCT/EP2016/068277, dated Oct. 20, 2016, WIPO, 6 pages.

*Primary Examiner* — Sharon A. Polk
(74) *Attorney, Agent, or Firm* — McCoy Russell LLP

(57) ABSTRACT

Direct printing machine for printing onto containers, with a conveyor for transporting the containers in container receptacles along a transport path, and with several printing stations which are respectively associated with the container receptacles and which are each formed with several separately adjustable direct print heads for printing several partial prints of a print onto a container, wherein the printing stations are each associated with their individual inspection device with at least one camera to inspect the position of the partial prints on the container.

20 Claims, 4 Drawing Sheets

(51) Int. Cl.
*B41J 2/045* (2006.01)
*B41J 11/00* (2006.01)
*B41J 25/308* (2006.01)
*B41M 5/00* (2006.01)
*B65B 61/02* (2006.01)
*H04N 5/232* (2006.01)
*H04N 5/369* (2011.01)
*G06T 7/00* (2017.01)

(52) U.S. Cl.
CPC ......... *B41J 2/04581* (2013.01); *B41J 11/007* (2013.01); *B41J 25/308* (2013.01); *B41M 5/0088* (2013.01); *B65B 61/025* (2013.01); *G01N 21/909* (2013.01); *H04N 5/23296* (2013.01); *H04N 5/3692* (2013.01); *G06T 7/0004* (2013.01); *G06T 2207/30168* (2013.01)

(58) Field of Classification Search
CPC . B41J 25/308; H04N 5/3692; H04N 5/23296; B65B 61/025; B41M 5/0088; G06T 7/0004; G06T 2207/30168
See application file for complete search history.

(56) References Cited

U.S. PATENT DOCUMENTS

| | | |
|---|---|---|
| 9,522,758 B2 | 12/2016 | Grote et al. |
| 9,649,856 B2 | 5/2017 | Lindner et al. |
| 2008/0034990 A1 | 2/2008 | Hilpert et al. |
| 2012/0151883 A1* | 6/2012 | Klarl ................... B65G 47/244 53/558 |

FOREIGN PATENT DOCUMENTS

| | | | |
|---|---|---|---|
| DE | 102007050490 A1 | | 4/2009 |
| DE | 102011001127 A1 * | 9/2012 | ............ B07C 5/126 |
| DE | 102012209305 A1 | | 12/2013 |
| EP | 1769916 A2 | | 4/2007 |
| EP | 1918100 A2 | | 5/2008 |
| EP | 2639069 A1 | | 9/2013 |
| EP | 2860515 A1 | | 4/2015 |
| WO | 03106177 A2 | | 12/2003 |
| WO | 2012022746 A1 | | 2/2012 |

* cited by examiner

DIRECT PRINTING MACHINE AND METHOD FOR PRINTING CONTAINERS USING DIRECT PRINTING

CROSS-REFERENCE TO RELATED APPLICATIONS

The present application is a U.S. National Phase of International Patent Application Serial No. PCT/EP2016/068277 entitled "DIRECT PRINTING MACHINE, AND METHOD FOR PRINTING CONTAINERS USING DIRECT PRINTING," filed on Aug. 1, 2016. International Patent Application Serial No. PCT/EP2016/068277 claims priority to German Patent Application No. 10 2015 216 026.2, filed on Aug. 21, 2015. The entire contents of each of the abovementioned applications are hereby incorporated by reference in their entirety for all purposes.

TECHNICAL FIELD

The invention relates to a direct printing machine and a method for printing a direct print onto containers.

BACKGROUND AND SUMMARY

It is known that containers, such as bottles or cans, are provided with a direct print for individual identification marking of the container contents, where differently colored printing inks are applied with multiple direct print heads directly onto the container in several passes. The containers are transported in container receptacles of a conveyor for printing and applied a surface print using the direct print heads. Such a direct print head is, for example, an ink jet print head having a plurality of nozzles typically arranged in one or more rows on the direct print head. For surface printing, a rotational motion of the container with the container receptacle about its longitudinal axis and/or a pivoting motion of the direct print head substantially perpendicular to the nozzle row is additionally performed. The print image itself is present as a digital image in a computer control system for controlling the direct print heads or container receptacles, respectively. Furthermore, the printing ink is cured in a subsequent curing device with UV or electron beams by cross-linking.

An apparatus and a method for printing onto containers are known from WO 2012 0/022746 in which several treatment stations, each with several print heads are arranged on a rotary machine in which the containers are moved with transport elements along a suitable path to the individual print heads.

Furthermore, an apparatus and a method for printing onto containers is known from DE 10 2007 050 490 A1 in which the containers are transported by a rotor and printing stations arranged thereon are each printed on by a plurality of print heads [sic]. The print heads can be switched toward and away from a printing position for changing a print head or a changing a partial print. The direct print is inspected in the runout region of the rotor by way of an optoelectronic inspection system.

However, the print heads in such direct printing machines must typically always be adapted to different container sizes. The disadvantage there is that the individual print heads must be adjusted relative to each other with correspondingly high precision due to the high demand regarding the quality of the direct print. For example, the pixel resolution of a direct print is $3/100$ mm, and consequently, the direct print heads need to be adjusted more precisely by about an order of magnitude in order to produce a high quality print image. It has shown that this requires a significant effort when setting up the direct printing machine, for example, by repeatedly creating test prints and then performing manual fine adjustment of the direct print heads.

The object of the present invention is therefore to provide a direct printing machine and a method for printing a direct print onto containers in which the adjustment of the direct print heads in the machine device is less complex and therefore inexpensive.

To satisfy this object, the invention provides a direct printing machine.

Due to the fact that the printing stations with the separately adjustable direct print heads are each associated with their individual inspection device with at least one camera, the container can be captured and inspected by the camera after the application of a partial print. Consequently, the individual partial prints can be inspected separately from each other and therefore be inspected better during the inspection. In addition, a particularly accurate and structurally simple combination can be selected by associating the camera with the printing station, which entails particularly lower tolerances. As a result, the position of the partial prints on the container can be inspected particularly accurately and associated with the position of the respective direct print head. Consequently, the overall position of the individual partial prints on the container can therefore be determined with high precision and reliability, so that the direct print heads can be adjusted based thereupon in a particularly simple and therefore inexpensive manner.

The direct printing machine can be arranged in a beverage processing system. The direct printing machine can be arranged downstream of a filling system for filling a product into the containers and/or downstream of a capper. The direct printing machine, however, can also be upstream of the filling process and/or be directly downstream of a container manufacturing process.

The containers can be provided to receive beverages, hygiene products, pastes, chemical, biological and/or pharmaceutical products. The container can generally be provided for any flowable or fillable media. The containers can be made of plastic material, glass or metal, but also be made of PET, PEN, HD-PE or PP.

Furthermore, containers with material mixtures are conceivable. The containers can be bottles, cans, and/or tubes.

The conveyor can be formed as a carousel which is rotatable about a vertical axis. "Vertical" can presently mean that this is the direction that is directed toward the center of the earth. The container receptacles can be arranged on the circumference of the carousel or the conveyor, respectively. The conveyor can also be formed with any other suitable self-contained transport path on which the container receptacles are arranged.

The container receptacles can be configured to move and/or rotate the containers during printing relative to the direct print heads. The container receptacles can, in particular, be configured to displace the containers perpendicularly and/or parallel to a direction of printing of the direct print heads. "Direction of printing of the direct print heads" can presently mean that this is the ejection direction of the print droplets from the direct print heads of a printing station onto the container that are to be applied a print. The container receptacles can each comprise a centering bell, a turntable, a positioning unit and/or a direct drive.

The container receptacles can each be arranged directly on the associated printing station. In other words, the direct print heads of a printing station can form a unit with the associated container receptacle. It is also conceivable that the respective container receptacle is part of the associated printing station.

The several separately adjustable direct print heads can be arranged in the printing station via a support, a positioning unit or the like. The direct print heads can operate with a digital or inkjet printing method, such as drop on demand, where the ink is delivered to the container by use of a plurality of print nozzles. "Ink-jet printing method" can presently mean that a sudden pressure increase is created in the chambers of a print nozzle by way of a piezo-electric or thermal element such that a small amount of ink print is forced through the print nozzle and delivered as a droplet onto the container. The direct print head can comprise a plurality of print nozzles in a range from 100 to 10,000 nozzles, in particular, in a range from 500 to 1,100 nozzles. The print nozzles can be arranged in one or more nozzle rows (for example 1-4) which are arranged, in particular, parallel to the container axis. The several separately adjustable direct print heads can also be configured as an integrally formed unit in which the print nozzles are arranged in several separately adjustable nozzle plates. "Separately adjustable" can presently mean that the direct print heads and/or the nozzle plates are each displaceable and/or rotatable. Each of the direct print heads can be displaceable and/or rotatable about one, two or three axes. Adjustment screws can be provided to adjust the direct print heads. For example, the direct print heads can be arranged on a common support that comprises an adjustment mechanism. It is also conceivable that the adjustment mechanism is formed with controllable actuators. The images of the camera can there be evaluated and parameters for controlling the adjustment mechanism can be calculated therefrom.

"Partial prints" can presently mean that this corresponds to a printing portion of the respective direct print head of a printing station in one print color. The print colors can presently be, for example, black, white, cyan, magenta or yellow or any other type of print color combination. In other words, the printing stations can each be configured to print all the colors of the direct print onto the container, each with a direct print head.

The fact that the "printing station is respectively associated with its individual inspection device with at least one camera" can presently mean that each printing station comprises a camera for inspection and/or adjustment. For example, a direct printing machine with a conveyor comprising 12 container receptacles then comprises 12 printing stations and 12 cameras.

It is conceivable that the camera comprises a matrix or line sensor for image recording and a lens. The inspection device can further comprise or be connected to an image processing device. It is conceivable that each inspection device of the direct printing machine comprises its individual image processing device or that all inspection devices are connected to one image processing device. The image processing devices can respectively be integrated into the cameras. The printing stations can be configured with inductive energy and/or data transmission units in order to supply their respective inspection device and preferably the camera with energy and/or to transmit their data, respectively.

"Position of the partial prints on the container" can presently mean that this is the position of the partial prints on the container. Likewise or additionally, this can mean that this is the positions of the respective individual partial prints, the position or the positions of a combination of several partial prints and/or the position of all partial prints together on the container (for example, the entire print image). Likewise or additionally, this can mean that this is the position of the partial prints relative to each other on the container and/or on a wound-off container surface. The position of the partial prints on the container can be inspected with the inspection device over a partial region or over the entire 360° circumference of the container.

The camera can be movable by a positioning unit which preferably comprises a linear motor. This makes it possible to move the camera to one or more inspection positions so that the partial prints are inspected from the best possible viewing direction. For example, the positioning unit can be configured to move the camera to inspection positions corresponding to the print positions of the direct print heads. As a result, the partial prints are each inspected from the same viewing direction directly during or after printing. It is also conceivable that the camera can be moved to individual regions of the partial print using the positioning unit, so that they can be greatly enlarged, for example, with a macro or microscope lens. The linear motor can comprise a long stator and a runner with a roller guide. The inductive energy and/or data transmission unit for the inspection device, in particular for the camera, can preferably be integrated into the linear motor.

The positioning unit can be configured to move the associated container receptacle together with the camera relative to the direct print heads. A positioning unit already being used to move the container receptacles can additionally be used to move the camera. Consequently, the costs for the positioning unit are particularly low. For example, the printing stations can each comprise the direct print heads and the positioning unit with the container receptacle and with the camera. It is then possible using the positioning unit to move the container receptacle together with the camera to the respective direct print heads along a path, so that the container is inspected directly after the application of the respective partial print. For example, the separately adjustable direct print heads can be arranged at least in part vertically above one another and perpendicular to the transport path. The positioning unit can then move the container receptacle and the camera, respectively, vertically relative to the direct print heads.

It is also conceivable that the positioning unit is configured to move the direct print heads together with the camera relative to the associated container receptacle. Here as well, the costs for the positioning unit are particularly low, since the already existing positioning unit for the direct print heads can be used. Furthermore, the camera is then fixedly adjusted relative to the direct print heads and operates very precisely. For example, the conveyor can be configured as a carousel with container receptacles and the printing stations, where the direct print heads of a printing station can each be moved together with the camera by positioning unit parallel to the transport path. The camera can then be moved by the positioning unit relative to the container receptacle to an inspection position between or after all partial prints in order to inspect the partial prints or the entire direct print.

The positioning unit can be configured to move the camera longitudinally, radially and/or tangentially relative to an axis of rotation of the container receptacle, in particular synchronously or in a constant relationship relative to a motion of the container receptacle. As a result, the camera can be used in a particularly flexible and precise manner for the inspection. For example, due to the motion longitudinally or tangentially relative to the axis of rotation, a larger partial print can be inspected than would be allowed by the field of view of the camera alone. The focus of the camera can be adjusted due to the radial motion, which makes the inspection of the partial print very accurate.

The camera can comprise a line sensor, and the positioning unit and/or container receptacle can be configured to move the camera and/or the container such that a relative motion transverse to the line sensor between the camera and a container surface is substantially constant during inspection. As a result, a line sensor can be used with the camera and a two-dimensional image can be generated by way of the relative motion. As a result, the camera is simpler in design and captures the respective partial prints in sections vertically and at the same distance from the container surface. Consequently, a particularly accurate inspection of the partial prints is performed in a simple manner.

The positioning unit can be configured to move the camera in parallel and/or transversely to the transport path, in particular synchronously or in a constant relationship to a transport motion of the conveyor. As a result, the transport motion of the conveyor can be compensated for or used to record different viewing directions onto the container.

The direct print heads and the camera can be located on mutually opposite sides of the transport path. This allows one or more direct print heads to print on one side of the container, and the camera can inspect a portion in a particularly efficient manner that is already printed on the opposite side of the container.

The conveyor can be a carousel with a circular transport path, where the direct print heads are disposed on the transport path on the outside and the camera on the inside. This can also be reversed, so that the direct print heads are arranged inside and the cameras outside.

The inspection device can comprise a protective housing for the camera. As a result, the camera is particularly effectively shielded from the influence of coloring or UV from the printing station. The protective housing can comprise a closure and/or a protective pane. The closure can be opened during the inspection and then closed again. Furthermore, the protective pane can be coated to avoid light reflections.

The inspection device can comprise a laser module for triangulating 3D points on the surface of the container. As a result, for example, embossings or seams on the container can be better recognized. Consequently, the orientation of the container in the container receptacle can be captured and used for printing or inspecting the partial print and/or the direct print.

The inspection device can comprise an illumination device, in particular a ring light around a lens of the camera and/or a luminescent screen for illuminating through the container. As a result, container structures such as embossings and other identifying features can be particularly well recognized prior to printing and the container can be oriented therewith. The container can be illuminated particularly uniformly during the inspection by way of an illumination device, such as the ring light. As a result, particularly high dynamics with respect to the printed image are obtained, so that the inspection can be conducted very accurately and reliably.

The illumination device can comprise a bright and/or dark field illumination unit. The partial prints can be captured particularly well using the bright field illumination unit. The dark field illumination unit can presently mean that the light of the illumination unit is directed only indirectly onto the camera by way of refractions and/or scatters on the container and no direct light then enters the camera. As a result, elevations, such as an embossing or a press seam on the container can be better detected. The dark field illumination unit can be configured, for example, as a line-shaped illumination unit.

It is also conceivable that the illumination device is configured for illumination with different spectral components in order to increase the contrast when inspecting the partial print. The illumination device can comprise, for example, LEDs of different colors. As a result, the light of the illumination device can be adapted to the color of the partial prints.

The container receptacles can each be formed with a rotary position sensor. As a result, the container can be captured with the camera particularly easily along its circumference by a rotation about the former's longitudinal axis. A rotational position of a turntable of the container receptacle can be captured with the rotary position sensor. For this purpose, the camera can preferably comprise a line sensor which is arranged, in particular, parallel to an axis of rotation of the rotary position sensor. A rotation of 360° can then be performed with the container receptacle, so that the container is captured fully circumferentially by the line scan camera. The rotary position sensor can be configured as an absolute or an incremental sensor. For capturing the rotational position of the turntable, the rotary position sensor can be connected to a motor or a machine control unit. It is also conceivable that the rotary position sensor is integrated into a servomotor. The resolution of the rotary position sensor can be in a range of 2000-5000, preferably 4000-5000 pulses per revolution. The partial prints can then be captured at a high resolution, so that their orientation can accordingly be adjusted precisely.

The inspection device can be configured to capture an orientation of the container in the container receptacle using the camera and/or the rotary position sensor. Elevations on the container can preferably be captured with the camera and the dark field illumination unit, such as, for example, an embossing, a press seam or the like. As a result, the container can be aligned relative to the printing station when running in and still prior to being applied a print. It is also conceivable that the inspection device is configured to determine a starting point of one or more subsequent partial prints in the circumferential and/or longitudinal direction of the container by way of the position of a partial print that is already printed onto the container.

The direct print heads and/or the camera can have a modular design, so that the modules are particularly easy to exchange without tools. For this purpose, the supply lines can be provided with quick-release couplings that are quickly manually exchangeable.

In addition, the invention provides a method for printing onto containers.

Due to the fact that a container in a printing station is provided with several partial prints of a direct print using several adjustable direct print heads, for example, different print colors of the direct print can be applied particularly precisely relative to one another onto the container. Due to the fact that the position of the partial prints on the container is inspected with at least one camera by an inspection device individually associated with the printing station, the tolerances between the camera and the printing station are particularly low. As a result, particularly high accuracy in the inspection is obtained, so that the direct print heads can be aligned relative to each other in a particularly simple and accurate manner.

The method can be carried out with a direct printing machine having the features described above. The method can comprise providing a direct printing machine for printing a direct print onto containers.

During the inspection, the camera can be moved in a manner synchronized to the container movement, so that a container surface in a camera image moves at a constant speed or is still. This allows the camera to be used for inspection while the container receptacle moves. Due to a uniform speed of the container surface and the camera, the use of a line sensor is also possible with which the motion is perpendicular to the sensor line. As a result, the camera is of a particularly simple configuration and can be aligned to the viewing direction such that it is as perpendicular as possible to the container surface. Consequently, the container surface is resolved particularly accurately.

The container can be aligned relative to the printing station with the aid of the inspection device prior to being applied a print. This allows the method to be used even more efficiently. It is presently conceivable that container structures are detected by the inspection device or the camera, respectively, for example, embossings, seams or the like. This makes it possible to additionally use the inspection device as an alignment aid.

It is also conceivable that the camera is moved by a positioning unit to inspection positions at which a respective partial print or the entire direct print is inspected.

In addition, the camera can be referenced by use of the positioning unit. For example, the container receptacle and/or a part of the container receptacle and/or a marking on the container receptacle can be recognized by way of image recognition and used as a reference point for the position of the camera relative to the container receptacle. It is also possible that the camera captures one or more of the direct print heads for referencing. For this purpose, the camera can capture one or more direct print heads, a part thereof, or a marking on a direct print head. As a result, tolerances in the container receptacle or in the positioning unit can be compensated. In addition, it is possible to evaluate an edge of a partial print or of the entire direct print and to take its distance from the container support as a nominal height.

A starting point of one or more subsequent partial prints in the circumferential and/or longitudinal direction of the container can be determined by way of a partial print that is already printed onto the container. As a result, the inspection device can also be employed to align the containers in the printing station. It is conceivable that fine positioning of the direct print relative to the print nozzles is determined in the longitudinal direction using the starting point. In other words, it can be determined at which print nozzle the print commences, i.e., a little higher toward the neck or slightly lower toward the base of the container.

The printing distances of the adjustable direct print heads can be determined by way of inspecting the partial prints. This improves the sharpness and thus the contrast of the printed image. For example, the focus can be adjusted via the aforementioned radial movement of the camera, whereby the distance of the camera from the container surface is determined. In a further step, a distance of the direct print heads from the container surface can then be adjusted based on the distance of the camera.

In addition, the method can comprise the above-described features of the direct printing machine individually or in any combination.

BRIEF DESCRIPTION OF FIGURES

Further features and advantages of the invention shall be explained in more detail below with reference to the embodiments illustrated in the figures.

DETAILED DESCRIPTION

Figure 1:
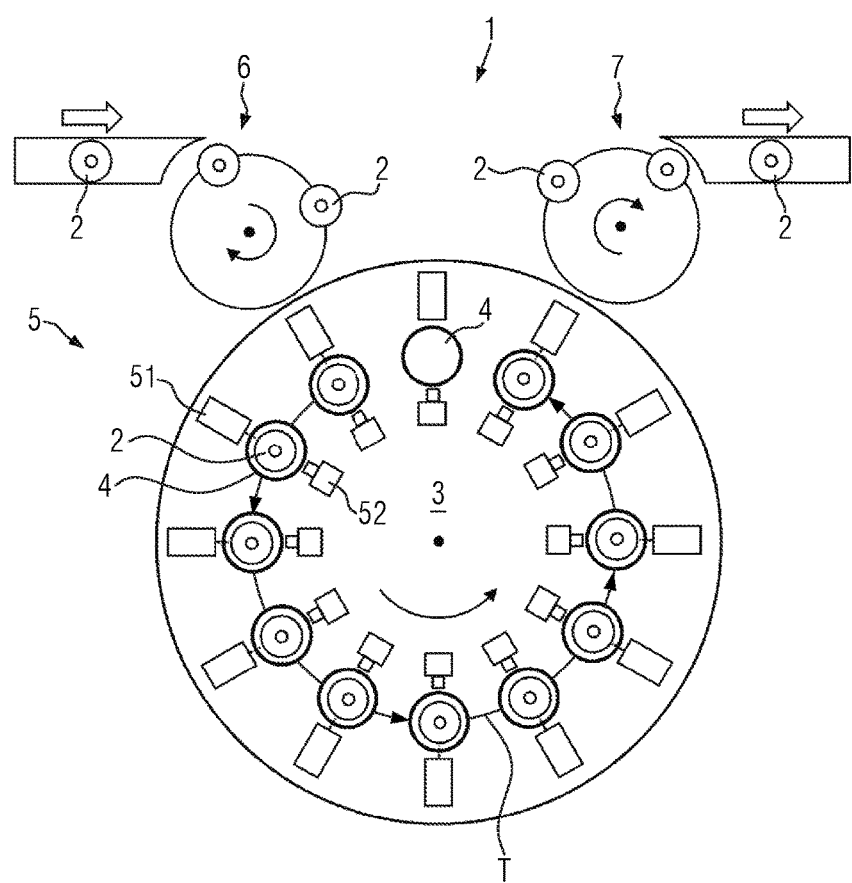
FIG. 1 shows an embodiment of a direct printing machine in a top view.

FIG. 1 shows a top view of an embodiment of a direct printing machine 1 for printing onto containers 2. It can be seen that containers 2 are transferred by an infeed starwheel 6 to conveyor 3 that is configured as a arousel. Conveyor 3 is configured to transport containers 2 in container receptacles 4 along transport path T. It can be seen that each container receptacle 4 is associated with a printing station 5, each comprising several separately adjustable direct print heads 51 for printing several partial prints onto containers 2, for example, using multiple print colors. Furthermore, each printing station 5 is associated with its individual inspection device with a camera 52. Direct print heads 51 and camera 52 are presently arranged, for example, opposite one another on the sides of transport path T. As a result, direct print heads 51 can print onto one side of container 2 and camera 52 can inspect the other side with the already completed print portion. However, any other suitable arrangement of direct print heads 51 or camera 52, respectively, is also conceivable.

After being transferred by infeed starwheel star 6, container 2 is introduced into a container receptacle 4 and associated printing station 5 and transported by conveyor 3 along transport path T. After all partial prints have been applied, container 2 is transferred to discharge starwheel 7 and transported to further treatment stations, for example, to a packaging machine.

Figure 2A:
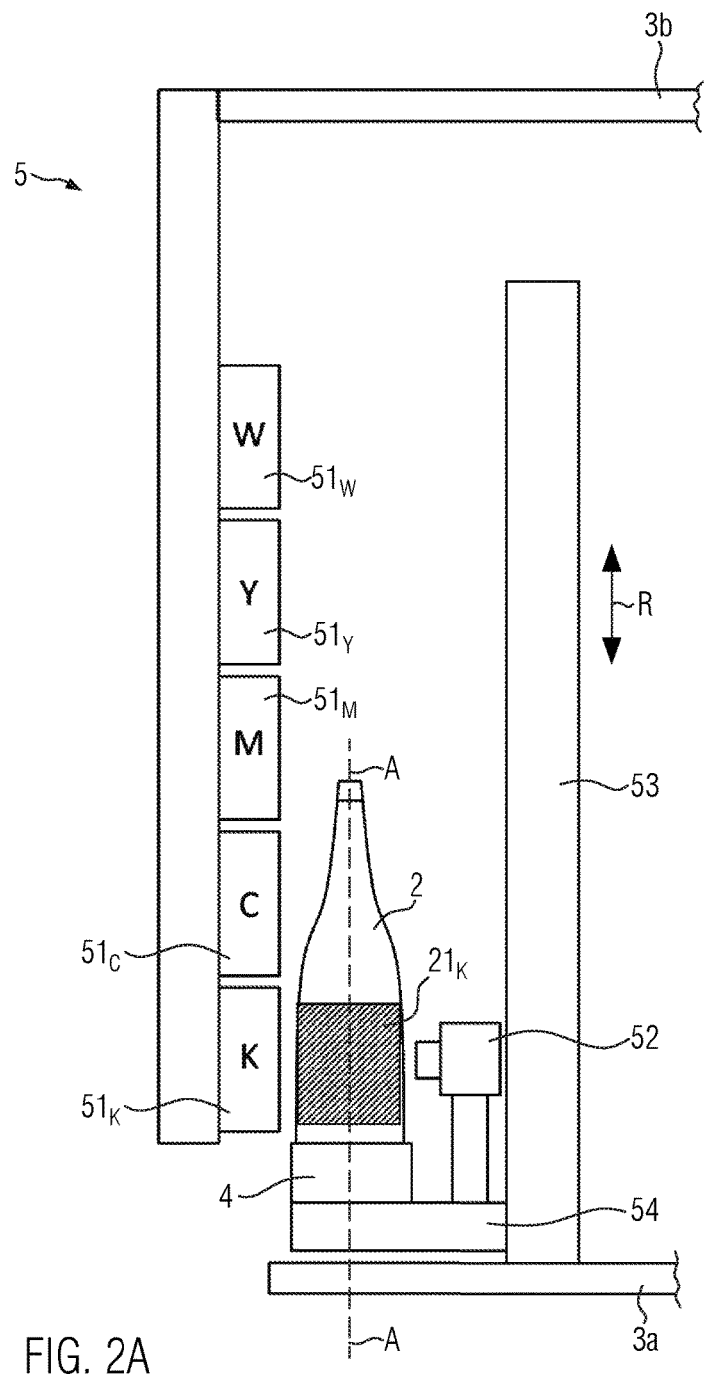
FIG. 2A shows an embodiment of a printing station of the direct printing machine of FIG. 1 in a lateral view when printing a first partial print.

The exact configuration of printing station 5 shall now be described in more detail with reference to FIG. 2A:

FIG. 2A illustrates in more detail an embodiment of printing station 5 of direct printing machine 1 according to preceding FIG. 1 in a lateral view. Carousel support 3a can be seen, on which positioning unit 53 for container receptacle 4 and camera 52 are arranged. Positioning unit 53 is presently a linear unit with which boom 54 is movable vertically along direction R. It is conceivable, for example, that the linear unit comprises a long stator linear motor with which the energy and data transmission to camera 52 is additionally effected. Container receptacle 4 is further arranged on boom 54 and comprises a turntable which is driven by a servo motor and with which container 2 is rotatable about axis A of rotation. Furthermore, container receptacle 4 can also comprise a centering bell, presently not shown, for receiving and centering the container openings. Camera 52 is connected to boom 54 via a rigid support arm. It is also conceivable, however, that camera 52 is movable by a further positioning unit longitudinally, radially and/or tangentially relative to axis A of rotation of container receptacle 4.

Furthermore, second support 3b of conveyor 3 can be seen, on which direct print heads $51_K$, $51_C$, $51_M$, $51_Y$ and $51_W$ are arranged. Direct print head $51_K$ is configured to print a black partial print $21_K$ onto container 2. For this purpose, direct print head $51_K$ is formed with a nozzle row with print nozzles, each of which delivers digitally actuated individual droplets of ink onto container 2. A surface print is then created on container 2 due to a rotation of container 2 about axis A of rotation. Accordingly, the other direct print heads $51_C$, $51_m$, $51_y$, and $51_W$ are adapted to print the colors cyan, magenta, yellow and white in further partial prints onto container 2, as described below with reference to FIGS. 2B-E.

Camera 52 is further adapted to inspect partial print $21_K$ after printing with respect to its position. This is done, for example, by way of image processing in which individual features of partial print $21_K$ are captured and recognized.

Figure 2B:
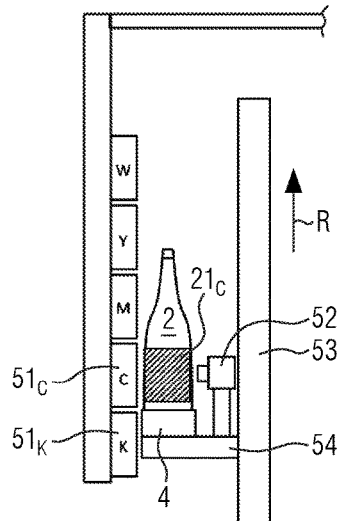
FIG. 2B shows an embodiment of a printing station of the direct printing machine of FIG. 1 in a lateral view when printing a second partial print.

As can further be seen from FIG. 2B, container receptacle 4 and container 2 located thereon are raised by positioning unit 53 in direction R after black partial print $21_K$ has been applied, so that container 2 is now disposed at the level of direct print head 51C, Container 2 is then rotated again and partial print $21_C$ is printed. When container 2 is rotated, the completed part of partial print $21_C$ is additionally captured by camera 52 and its position on container 2 is inspected.

Figure 2C:
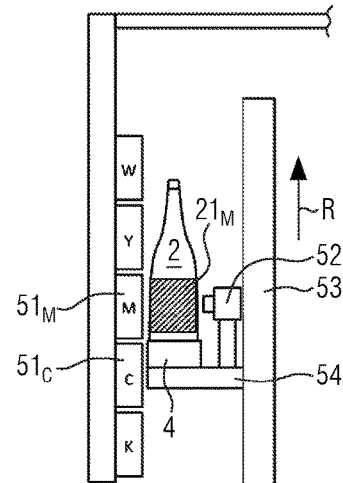
FIG. 2C shows an embodiment of a printing station of the direct printing machine of FIG. 1 in a lateral view when printing a third partial print.
Figure 2D:
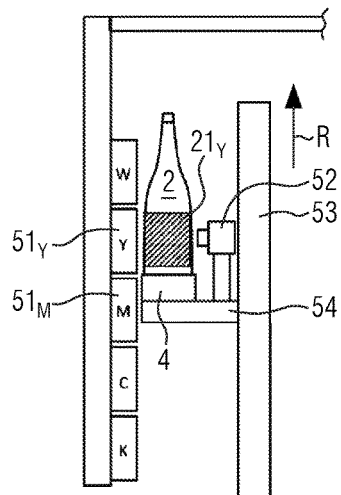
FIG. 2D shows an embodiment of a printing station of the direct printing machine of FIG. 1 in a lateral view when printing a fourth partial print.
Figure 2E:
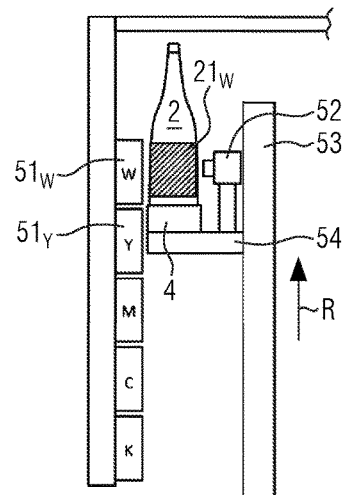
FIG. 2E shows an embodiment of a printing station of the direct printing machine of FIG. 1 in a lateral view when printing a fifth partial print.

The same procedure is then carried out according to FIGS. 2C-2E for the colors magenta, yellow and white in that container receptacle 4 and camera 52, respectively, are raised by positioning unit 53 to the printing positions of direct print heads $51_M$, $51_Y$, $51_W$ and applied a print. In addition, the position of partial prints $21_M$, $21_Y$, $21_W$ is also captured and inspected by camera 52.

In other words, after each printing step or during each printing step, respectively, the position of each individual partial print $21_K$, $21_C$, $21_M$, $21_Y$, $21_W$ is captured with camera 52 and the position is inspected. This makes it possible to inspect any maladjustment of direct print heads $51_K$-$51_W$ and to output individual values for adjustment. As a result, containers 2 are applied a print by direct printing machine 1 in FIG. 1 or at the printing stations of FIGS. 2A-2E, respectively, with a particularly high quality, yet the adjustment is supported in a quick and efficient manner. Consequently, the cost of tedious experimenting can be saved.

Figure 3:
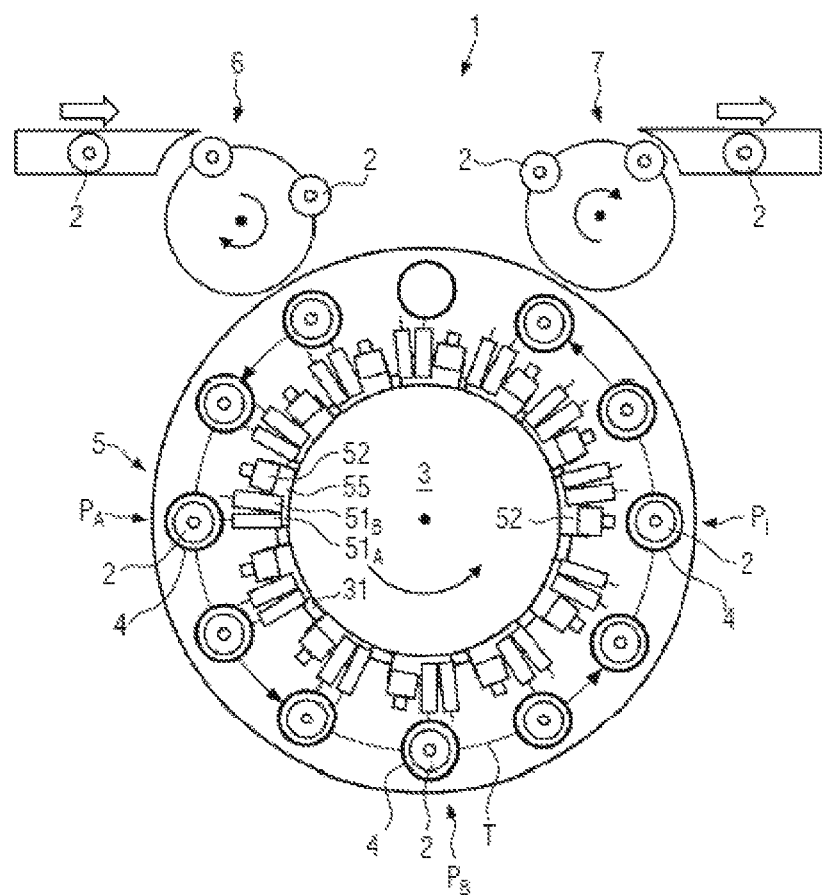
FIG. 3 shows a further embodiment of a direct printing machine in a top view.

FIG. 3 illustrates a further embodiment of a direct printing machine 1 in a top view. It differs from the embodiment in FIG. 1 essentially in that not container receptacles 4 but respective direct print heads $51_A$, $51_B$ and camera 52 are moved by positioning units 55.

It can be seen that containers 2 are first transferred by infeed starwheel 6 to conveyor 3, which is presently likewise configured as a carousel. Containers 2 are then transported in container receptacles 4 continuously along transport path T, are applied prints by printing stations 5, and then transferred to discharge starwheel 7.

It can further be seen that conveyor 3 is formed with a fixedly connected ring 31 on which several printing stations 5 are arranged. Printing stations 5 each comprise positioning unit 55, two or more direct print heads $51_A$, $51_B$ and a camera 52. Direct print heads $51_A$, $51_B$ together with camera 52 can be moved by positioning unit 55 tangentially relative to transport path T. The two direct print heads $51_A$ and $51_B$ of each printing station 5 are presently shown merely by way of example representing a plurality of direct print heads.

This makes it possible to move direct print head $51_A$ to position $P_A$ such that it is ready for printing and facing container 2 at position $P_A$. Container 2 is now rotated about its longitudinal axis and applied a partial print of a first color. At the same time, container 2 is continuously transported onward along transport path T. It is also conceivable, however, that conveyor 3 transports containers 2 intermittently.

If container receptacle 4 with container 2 is now disposed at position $P_B$, then direct print head $51_B$ is ready for printing with a second color. The container is again rotated about its longitudinal axis and applied the second partial print of the second color. During the further transport along transport path T, camera 22 is now moved by positioning unit 55 to the inspection position, which then faces container 2 at position $P_I$. Container 2 is now rotated by way of container receptacle 4 about its longitudinal axis and the two partial prints are inspected.

It is also conceivable that camera 52 is moved by positioning unit 55 to container 2 for inspection between the two positions $P_A$ and $P_B$ and the partial print of direct print head $51_A$ is inspected separately.

Here as well, the position can be inspected by inspecting the partial prints, and direct print heads $51_A$ and $51_B$ can then be adjusted quickly and accurately based thereupon.

Overall, direct printing machines 1 of FIGS. 1-3 are used as follows:

Containers 2 are transported in container receptacles 4 of conveyor 3 along transport path T and applied a print by printing stations 5 associated with container receptacles 4. One container 2 is applied several partial prints 21 of a direct print in each printing station 5 by several adjustable direct print heads 51. Furthermore, the position of partial prints 21 on container 2 is inspected with camera 52 associated specifically with printing station 5. This makes it possible to capture the position of individual partial prints 21 in a simple and highly accurate manner relative to direct print heads 51 and to adjust them based thereupon. The adjustment is therefore very accurate, simple and inexpensive.

The following further configurations are additionally possible for the embodiments of FIGS. 1-3 and in any combination:

Container 2 can be aligned relative to printing station 5 with the aid of the inspection device prior to being applied a print. This can be done, for example, based on container structures, such as embossings, seams or the like.

It is further conceivable that the inspection device comprises a protective housing for camera 52. As a result, camera 52 is better protected against the effects of the print color.

Furthermore, a laser module for triangulating 3D points on the surface of the container can be arranged in the inspection device. 3D structures of the container, such as embossings or seams can be better captured therewith.

Furthermore, it is also conceivable that the inspection device comprises an illumination device, such as a ring light around the lens of camera 52. In addition, a luminescent screen for illuminating container 2 can be arranged in the inspection device, so that container structures can be captured in the transmitted light.

It is understood that the features in the embodiments described above are not restricted to these specific combinations and are also possible in any other random combinations.

The invention claimed is:

1. A direct printing machine for printing onto containers, comprising:
   a conveyor for transporting said containers in container receptacles along a transport path; and
   several printing stations which are respectively associated with said container receptacles and which are each formed with several separately adjustable direct print heads for printing several partial prints of a direct print onto a container, wherein said printing stations are each associated with their individual inspection device with at least one camera to inspect a position of said partial prints on said container,
   where said at least one camera is movable by a positioning unit, and
   where said positioning unit is configured to move said associated container receptacle together with said at least one camera relative to said direct print heads.

2. The direct printing machine according to claim 1, where said positioning unit comprises a linear motor.

3. The direct printing machine according to claim 2, where said positioning unit is configured to move said at least one camera parallel and/or transversely to said transport path synchronously or in a constant relationship relative to a transport motion of said conveyor.

4. The direct printing machine according to claim 1, where said positioning unit is configured to move said at least one camera longitudinally, radially, and/or tangentially relative to an axis of rotation of said container receptacle.

5. The direct printing machine of claim 4, where said positioning unit is configured to move said at least one camera synchronously or in a constant relationship relative to a motion of said container receptacle.

6. The direct printing machine according to claim 1, where said at least one camera comprises a line sensor, and said positioning unit and/or said container receptacle are configured to move said at least one camera and/or said container such that a relative motion transverse to said line sensor between said at least one camera and a container surface is substantially constant during inspection.

7. The direct printing machine according to claim 1, where said direct print heads and said at least one camera are located on mutually opposite sides of said transport path.

8. The direct printing machine according to claim 1, where said conveyor is a carousel with said transport path, where said transport path is a circular transport path, and where said direct print heads are disposed on said transport path on an outside and said at least one camera on an inside or vice versa, respectively.

9. The direct printing machine according to claim 1, where said inspection device comprises a protective housing for said at least one camera.

10. The direct printing machine according to claim 1, where said inspection device comprises a laser module for triangulating 3D points on a surface of said container.

11. The direct printing machine according to claim 1, where said inspection device comprises an illumination device that is a ring light around a lens of said at least one camera and/or a luminescent screen for illuminating through said container.

12. The direct printing machine according to claim 11, where said illumination device comprises a bright and/or dark field illumination unit.

13. The direct printing machine according to claim 1, where said container receptacles are each formed with a rotary position sensor.

14. A method for printing a direct print onto containers, comprising:
   transporting said containers in container receptacles of a conveyor along a transport path; and
   applying a print by printing stations associated with said container receptacles, where several partial prints of a direct print are applied to a container in a printing station by several adjustable direct print heads, and wherein a position of said partial prints on said container is inspected by an individual inspection device with at least one camera associated with said printing station,
   where, prior to printing, said inspection device aids in aligning said containers relative to said printing station.

15. The method according to claim 14, where said at least one camera is moved during inspection in a manner synchronized to a container motion, so that a container surface in a camera image moves at a constant speed or is still.

16. The method according to claim 14, where a starting point of one or more subsequent partial prints in a circumferential and/or a longitudinal direction of said containers is determined by way of a position of the partial prints already printed onto said containers.

17. The method according to claim 14, where printing distances of said adjustable direct print heads are determined by way of inspecting said partial prints.

18. A direct printing machine for printing onto containers, comprising:
   a conveyor for transporting said containers in container receptacles along a transport path; and
   several printing stations which are respectively associated with said container receptacles and which are each formed with several separately adjustable direct print heads for printing several partial prints of a direct print onto a container, wherein said printing stations are each associated with their individual inspection device with at least one camera to inspect a position of said partial prints on said container,
   where said at least one camera is movable by a positioning unit, and
   where said positioning unit is configured to move said direct print heads together with said at least one camera relative to said associated container receptacle.

19. The direct printing machine according to claim 18, where said positioning unit is configured to move said at least one camera longitudinally, radially, and/or tangentially relative to an axis of rotation of said container receptacle.

20. The direct printing machine according to claim 19, where said positioning unit is configured to move said at least one camera synchronously or in a constant relationship relative to a motion of said container receptacle.

* * * * *

UNITED STATES PATENT AND TRADEMARK OFFICE
CERTIFICATE OF CORRECTION

| | | |
|---|---|---|
| PATENT NO. | : 10,279,600 B2 | Page 1 of 1 |
| APPLICATION NO. | : 15/753934 | |
| DATED | : May 7, 2019 | |
| INVENTOR(S) | : Georg Gertlowski and Peter Lindner | |

It is certified that error appears in the above-identified patent and that said Letters Patent is hereby corrected as shown below:

On the Title Page

Item (73)
Correct the Assignee City from "Neutrabling" to "Neutraubling"

Signed and Sealed this
Seventh Day of February, 2023

Katherine Kelly Vidal
*Director of the United States Patent and Trademark Office*